US009990571B2

(12) United States Patent
Kobayashi

(10) Patent No.: US 9,990,571 B2
(45) Date of Patent: Jun. 5, 2018

(54) MEDIA DETERMINING APPARATUS FOR DETERMINING TRANSPARENCY OF A MEDIA, A MEDIA TRANSPORT APPARATUS FOR DETECTING AN END POSITION OF THE MEDIUM AND PRINTING APPARATUS FOR CONTROLLING START OF PRINTING ON A PRINTING MEDIUM

(71) Applicant: Tsuyoshi Kobayashi, Yamanashi-ken (JP)

(72) Inventor: Tsuyoshi Kobayashi, Yamanashi-ken (JP)

(73) Assignee: CANON FINETECH NISCA INC., Misato-Shi, Saitama (JP)

( * ) Notice: Subject to any disclaimer, the term of this patent is extended or adjusted under 35 U.S.C. 154(b) by 0 days. days.

(21) Appl. No.: 14/801,207

(22) Filed: Jul. 16, 2015

(65) Prior Publication Data
US 2016/0019442 A1 Jan. 21, 2016

(30) Foreign Application Priority Data
Jul. 18, 2014 (JP) .................................. 2014-147866

(51) Int. Cl.
*G06F 3/12* (2006.01)
*G06K 15/02* (2006.01)
(Continued)

(52) U.S. Cl.
CPC ......... *G06K 15/023* (2013.01); *B41J 11/0095* (2013.01); *G06K 15/4065* (2013.01); *G01N 21/59* (2013.01)

(58) Field of Classification Search
CPC ....................... G06K 15/023; G06K 15/4065; G06F 3/1208; B65H 7/14
(Continued)

(56) References Cited

U.S. PATENT DOCUMENTS 4,983,854 A * 1/1991 Mizuno .................. B41J 11/009
250/223 R
6,153,888 A * 11/2000 Fournier ................. B65H 7/125
250/205
(Continued)

FOREIGN PATENT DOCUMENTS

JP H05-169037 A 7/1993
JP 2002-098650 A 4/2002
(Continued)

*Primary Examiner* — Gabriel Garcia
(74) *Attorney, Agent, or Firm* — Manabu Kanesaka

(57) ABSTRACT

To provide a media determining apparatus for enabling transparency of a medium to be determined at low cost, the media determining apparatus is provided with a transport section that transports a medium, a sensor including a light emitting device and a light receiving device to detect the medium, and a control section that detects the medium transported with the transport section corresponding to an output voltage of the sensor. The control section determines transparency of the medium by comparing the output voltage A of the sensor before a front end of the medium arrives at a detection position of the sensor, the output voltage B of the sensor when the front end arrives at the detection position, and the output voltage C of the sensor after the front end arriving at the detection position.

20 Claims, 8 Drawing Sheets

(51) Int. Cl.
    *G06K 15/00*    (2006.01)
    *B41J 11/00*    (2006.01)
    *H04N 1/04*    (2006.01)
    *G01N 21/59*    (2006.01)

(58) Field of Classification Search
    USPC ...... 358/1.1, 1.9, 1.13, 1.14, 1.15, 1.18, 498
    See application file for complete search history.

(56) References Cited

U.S. PATENT DOCUMENTS

| | | | |
|---|---|---|---|
| 9,253,347 B2 * | 2/2016 | Asai | H04N 1/00474 |
| 2005/0190368 A1 * | 9/2005 | Ehrhardt, Jr. | B65C 9/42 |
| | | | 356/431 |
| 2007/0091384 A1 * | 4/2007 | Lin | B41J 11/009 |
| | | | 358/474 |
| 2007/0138416 A1 * | 6/2007 | Ohta | B65H 7/14 |
| | | | 250/548 |
| 2013/0265361 A1 * | 10/2013 | Yatsunami | B41J 29/393 |
| | | | 347/19 |

FOREIGN PATENT DOCUMENTS

| | | |
|---|---|---|
| JP | 2008-218021 A | 9/2008 |
| JP | 2011-110778 A | 6/2011 |
| JP | 2013-158920 A | 8/2013 |

\* cited by examiner

Prior Art

Prior Art

MEDIA DETERMINING APPARATUS FOR DETERMINING TRANSPARENCY OF A MEDIA, A MEDIA TRANSPORT APPARATUS FOR DETECTING AN END POSITION OF THE MEDIUM AND PRINTING APPARATUS FOR CONTROLLING START OF PRINTING ON A PRINTING MEDIUM

TECHNICAL FIELD

The present invention relates to an apparatus for determining media, apparatus for transporting media and printing apparatus, and more particularly, to an apparatus for determining transparency of a medium, an apparatus for transporting media to detect a front end position of the medium, and a printing apparatus for performing printing processing on a printing medium.

BACKGROUND ART

Conventionally, a transparent media detection sensor for detecting transparent media (media having optical transparency including translucent media) has been known widely, and for example, in searching the Internet using "transparent media detection sensor" as a keyword, it is known that many sensors are commercially available.

As the transparent media detection sensor, there are various types such as a type using a reflector (regression reflector), for example, see Patent Document 1, a type of using a polarizer, for example, see Patent Document 2, and types of using a CCD sensor or line sensor, for example, see Patent Document 3. While such transparent media detection sensors have high accuracy, the sensors are susceptible to improvements in the cost.

In addition, in the field of business equipment, in consideration of the cost and requirement accuracy, sensors having a light emitting device (LED) and light receiving device (phototransistor) have been widely used. For example, Patent Document 4 discloses techniques for detecting a center portion of a printing area (label) temporarily attached to a continuous medium (label continuous medium) using a transmission sensor.

In this type of sensor, a sensor control circuit as shown in FIG. 12 is generally used. In other words, the anode side of a light emitting device Le (LED) is connected to Vcc (for example, +3.3 V), and the cathode side is connected to a collector of a transistor Tr1. The base of the transistor Tr1 is connected to an output terminal of an operational amplifier (OP) via a resistance R1, and a positive-phase input terminal of the operational amplifier (OP) is connected to a DA output port of a microprocessor MP via a DA converter (DA). Further, an emitter of the transistor Tr1 is connected to one end of a resistance R2 connected to a negative-phase input terminal of the operational amplifier (OP) and at the other end to a ground (hereinafter, abbreviated as GND). Therefore, by outputting the digital voltage from the microprocessor MP, it is possible to cause the light emitting device (Le) to emit light.

On the other hand, a collector of the phototransistor constituting the light receiving device Lr is connected to Vcc via a resistance R3, and an emitter is connected to GND. Further, the collector of the phototransistor is connected to an AD input port of the microprocessor MP with an AD converter incorporated. Therefore, the microprocessor MP is capable of capturing the output voltage of the collector of the phototransistor i.e. the output voltage output from the sensor control circuit (sensor Se).

In addition, as techniques related to the present invention, the inventor of the present invention proposed a printer capable of suppressing fluctuations in front end detection of media (see Patent Document 5).

PRIOR ART DOCUMENT

Patent Document

[Patent Document 1] Japanese Patent Application Publication No. 2008-218021
[Patent Document 2] Japanese Patent Application Publication No. 2002-098650
[Patent Document 3] Japanese Patent Application Publication No. H05-169037
[Patent Document 4]. Japanese Patent Application Publication No. 2011-110778
[Patent Document 5] Japanese Patent Application Publication No. 2013-158920

DISCLOSURE OF INVENTION

Problems to be Solved by the Invention

However, in the sensor control circuit as shown in FIG. 12, in the case of detecting in coexistence of a medium (hereinafter, referred to as "transparent body") that has optical transparency and a medium (hereinafter, referred to as "non-transparent body") that does not have optical transparency as a medium, it is difficult to detect the medium itself and discriminate between the media, and even when it is possible, there is the risk that misdetection occurs.

FIGS. 13 and 14 show the output voltage from the sensor control circuit (sensor) respectively when a medium is a white tube (non-transparent body) or transparent tube (transparent body) and the medium is transported between the light emitting device Le and the light receiving device Lr as shown in FIG. 12. In the figures, A is the output voltage before the medium is detected (before the medium arrives at a detection position of the sensor Se), C is the output voltage during detection of the medium, and E is the output voltage after detecting the medium (after the medium passing through the detection position of the sensor Se). As shown in FIG. 13, in the case of adjusting an emission amount of the light emitting device Le to be able to detect the non-transparent body, the output voltage C of the sensor control circuit is about 2.8 V (Vcc is +3.3V), it is possible to detect the non-transparent body by setting a threshold at a voltage e.g. 2.0 V sufficiently larger than the output voltages A and E (for example, 0.2 V). As shown in FIG. 14, however, in detecting the transparent body with the emission amount of the light emitting device Le when the non-transparent body is detected, the output voltage C is collapsed, and it is not possible to detect the transparent body itself (the output voltages A, E are not discriminated.).

In addition, the techniques of Patent Document 4 are excellent techniques for enabling a ' printing start position of a printing area to be detected automatically without directly detecting the entire position detection area or being dependent on the types' of sensor and printing sheets, but media require marking (general-purpose products are not used), and the techniques are susceptible to improvements in terms of running cost.

In view of the above-mentioned matter, a first object of the present invention is to provide a media determining apparatus for enabling transparency of a medium to be determined at low cost, a second object is to provide a media transport apparatus for enabling a front end position of a medium to be detected at low cost irrespective of whether the medium is transparent or non-transparent, and a third object is to provide a printing apparatus with high printing position accuracy on a printing medium at low cost irrespective of whether the medium is transparent or non-transparent.

Means for Solving the Problem

To attain the above-mentioned first object, a first aspect of the present invention is a media determining apparatus provided with a transport section that transports a medium, a sensor including a light emitting device and a light receiving device to detect the medium, and a control section that detects the medium transported with the transport section corresponding to an output voltage of the sensor, and the control section is characterized by determining transparency of the medium by comparing an output voltage A of the sensor before a front end of the medium arrives at a detection position of the sensor, an output voltage B of the sensor when the front end arrives at the detection position, and an output voltage C of the sensor after the front end arriving at the detection position.

In the first aspect, the control section may detect the output voltage B after detecting a voltage lower than the output voltage A. Further, the control section may determine that the medium is a transparent body when the output voltage C is higher than the output voltage A, while being lower than the output voltage B. Furthermore, the control section may classify the transparency of the medium by comparing a beforehand set threshold with the output voltage C. Still furthermore, the control section may determine that the medium is a non-transparent body when the output voltage C is higher than the output voltage B. Moreover, it is preferable that the sensor is a transmission sensor, and that the light emitting device and the light receiving device are arranged to be inclined with respect to a transport direction of the medium transported with the transport section or a direction orthogonal to the transport direction.

Further, to attain the above-mentioned second object, a second aspect of the present invention is a media transport apparatus provided with a transport section that transports a medium, a sensor including a light emitting device and a light receiving device to detect the medium, and a control section that detects the medium transported with the transport section corresponding to an output voltage of the sensor, and the control section is characterized by detecting a front end position of the medium by comparing an output voltage A of the sensor before a front end of the medium arrives at a detection position of the sensor, an output voltage B of the sensor when the front end arrives at the detection position, and an output voltage C of the sensor after the front end arriving at the detection position.

In the second aspect, the control section may detect the output voltage B after detecting a voltage lower than the output voltage A. Further, the control section may detect the front end position of the medium based on a transport amount of the medium with the transport section up to the present time from the time the front end of the medium arrives at the detection position of the sensor. Furthermore, the control section may detect a rear end position of the medium when an output voltage of the sensor is the same voltage as the output voltage A after detecting the output voltage C. Moreover, the sensor is comprised of a first sensor to detect transparency of the medium, and a second sensor disposed on the downstream side of the first sensor in a medium transport direction to perform front end detection of the medium, and the control section may determine transparency of the medium by comparing output voltages A to C of the first sensor to adjust an emission amount of a light emitting device constituting the second sensor corresponding to a result of determination. At this time, it is preferable that the first sensor is a transmission sensor, and that the light emitting device and the light receiving device constituting the first sensor are arranged to be inclined with respect to the transport direction of the medium transported with the transport section or a direction orthogonal to the transport direction.

Furthermore, to attain the above-mentioned third object, a third aspect of the present invention is a printing apparatus provided with a transport section that transports a printing medium, a sensor including a light emitting device and a light receiving device to detect the printing medium, a printing section that performs printing processing on the printing medium, and a control section that detects the printing medium transported with the transport section corresponding to an output voltage of the sensor, and the control section is characterized by controlling a start of printing on the printing medium by comparing an output voltage A of the sensor before a front end of the printing medium arrives at a detection position of the sensor, an output voltage B of the sensor when the front end arrives at the detection position, and an output voltage C of the sensor after the front end arriving at the detection position.

In the third aspect, the control section may compare the output voltages A to C to determine transparency of the printing medium and change a printing condition on the printing medium with the printing section.

Advantageous Effect of the Invention

It is possible to obtain effects that according to the first aspect of the present invention, using the sensor including the light emitting device and light receiving device, the control section compares output voltages A to C of the sensor to determine transparency of the medium, thereby enabling the transparency of the medium to be detected at low cost, that according to the second aspect, using the sensor including the light emitting device and light receiving device, the control section compares output voltages A to C of the sensor to detect the front end position of the medium, thereby enabling the front end position of the medium to be detected at low cost irrespective of whether the medium is transparent or non-transparent, and that according to the third aspect, using the sensor including the light emitting device and light receiving device, the control section compares output voltages A to C of the sensor to control a start of printing on the printing medium with the printing section, thereby enabling high printing position accuracy to be ensured on the printing medium at low cost irrespective of whether the medium is transparent or non-transparent.

BRIEF DESCRIPTION OF DRAWINGS

FIG. 10A illustrates an attachment for label cassette, and FIG. 10B illustrates an attachment for tube;

BEST MODE FOR CARRYING OUT THE INVENTION

An Embodiment in which the present invention is applied to a media determining apparatus for determining transparency of a medium will be described below. In addition, in order to simplify the description below, an example of using a tube as the medium will be described.
(Configuration)

Figure 1:
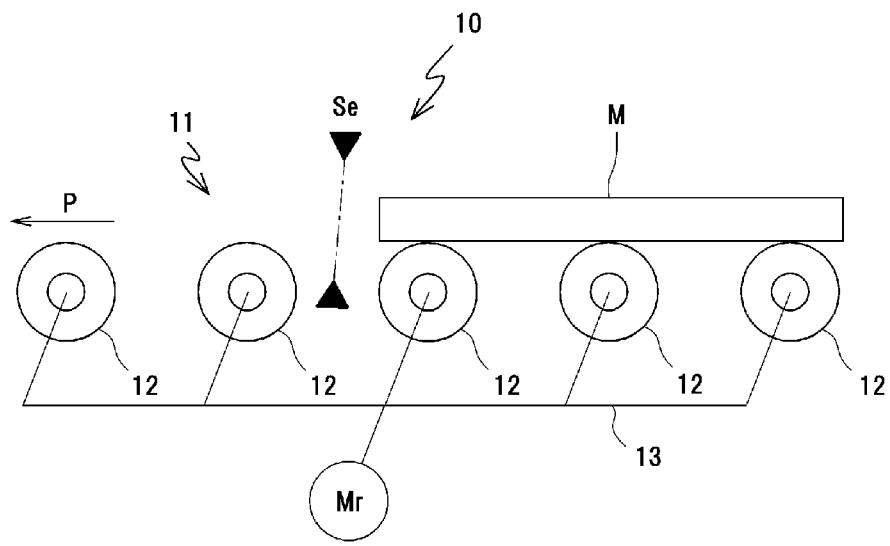
FIG. 1 is a side elevational view schematically illustrating a configuration of a media determining apparatus of an Embodiment to which the present invention is applicable.

As shown in FIG. 1, a media determining apparatus 10 of this Embodiment is provided with a transport section 11 that transports a tube as a medium. The transport section 11 has a plurality of rollers 12 provided at predetermined intervals to transport the medium M, a gear unit 13 (shown by tie lines schematically in FIG. 1), and a stepping motor Mr that supplies a rotation drive force to the gear unit 13.

The plurality of rollers 12 constitutes a transport path P to transport the medium M from the right to the left as viewed in FIG. 1. A sensor Se to detect the medium M is disposed to sandwich the transport path P. The sensor Se is a transmission sensor (also see FIG. 12) comprised of a light emitting device Le (LED) and a light receiving device Lr (phototransistor), and in this Embodiment, in order to enhance detection accuracy for the medium M, the light emitting device Le and light receiving device Lr (virtual line joining the devices i.e. optical axis) are arranged to be inclined with respect to a transport direction of the medium M transported with the transport section 11 and a direction orthogonal to the transport direction.

Figure 12:
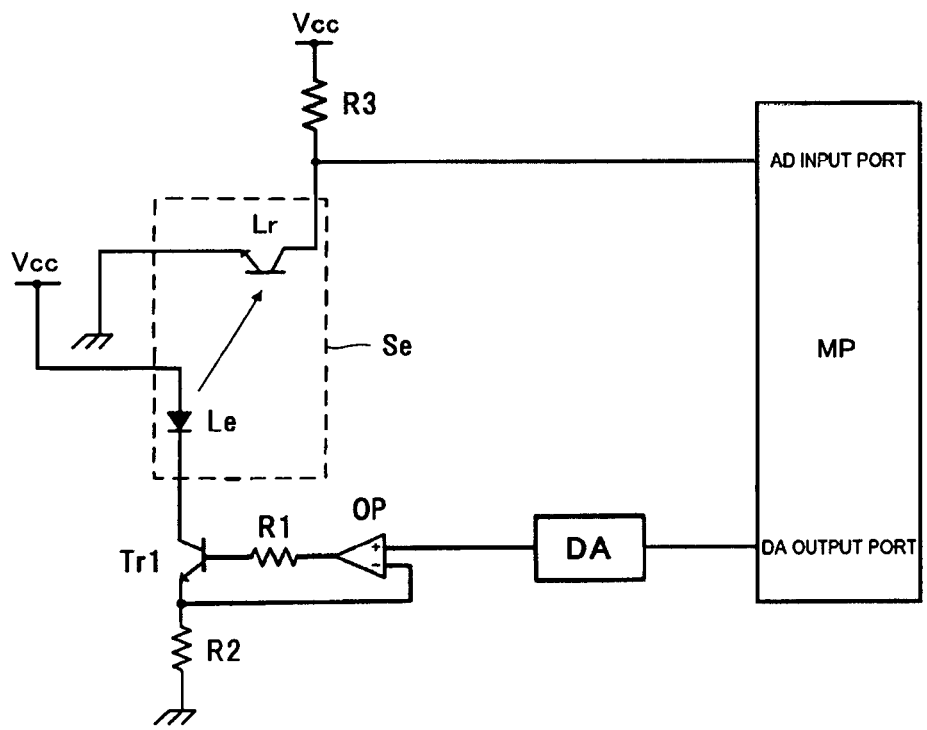
FIG. 12 is a circuit diagram of the sensor control circuit.

Further, the media determining apparatus 10 is provided with a microprocessor MP (control section) that detects the medium M transported with the transport section 11 corresponding to the output voltage output from the sensor control circuit as shown in FIG. 12. The microprocessor MP has a CPU, ROM, RAM and others and is comprised thereof, and the CPU, ROM and RAM are connected with internal buses.

The microprocessor MP is connected to external buses. The external buses are connected to an input control section to control an input section having a numeric keypad and enter button to input commands to the microprocessor MP, a display control section that controls a display section such as a liquid crystal display apparatus, a sensor control section, and a driver that controls operation of the stepping motor Mr.
(Transparency Determining Principles)

Described next are principles of determining transparency of the medium M by the media determining apparatus 10 of this Embodiment.

Figure 13:
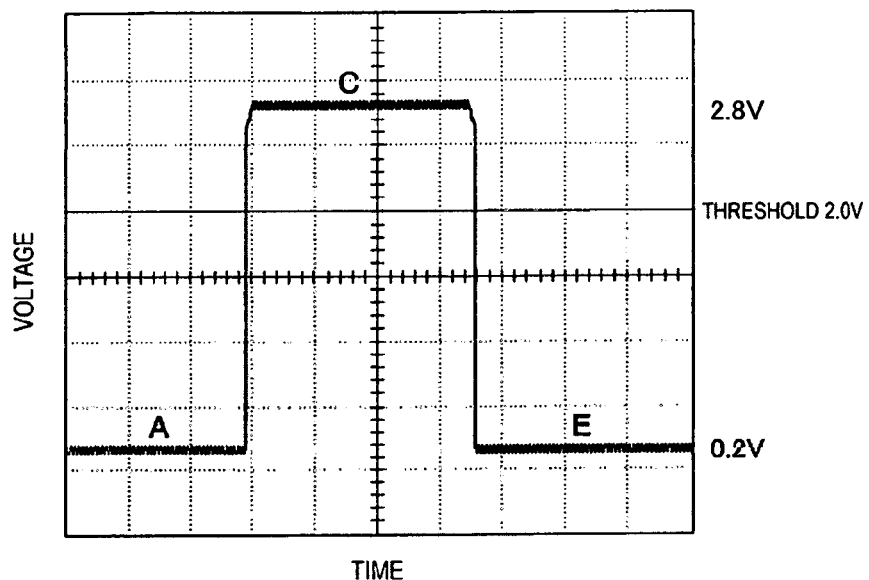
FIG. 13 is a graph schematically showing the output voltage output from the sensor control circuit when a medium is a white tube and is transported between a light emitting device and a light receiving device.
Figure 14:
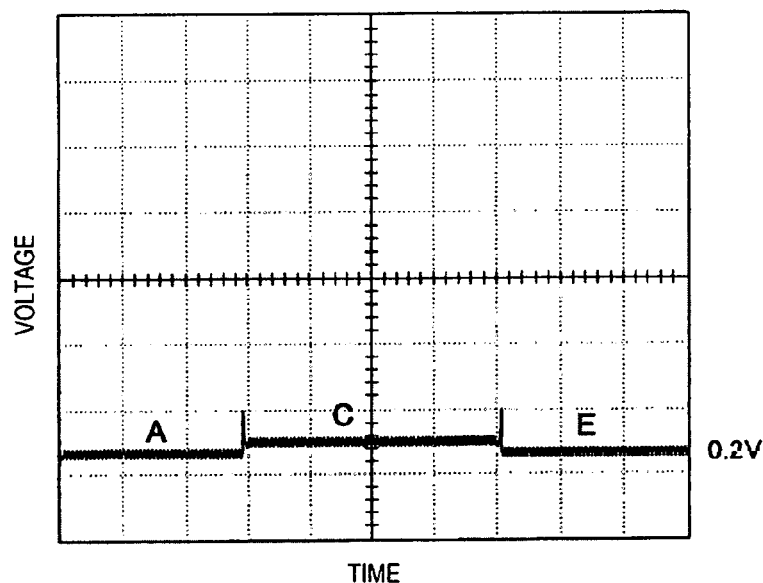
FIG. 14 is a graph schematically showing the output voltage output from the sensor control circuit when a medium is a transparent tube and is transported between the light emitting device and the light receiving device.

As shown in FIGS. 13 and 14, in detecting the transparent body (transparent tube in this example) with an emission amount of the light emitting device Le when the non-transparent body (white tube in this example) is detected, the output voltage C is collapsed, and it is not possible to detect the transparent body itself. Therefore, in this Embodiment, first, in order to enable the output voltage C during medium detection and the output voltage A before the medium detection. (and the output voltage E after the medium detection) to be identified, adopted is a configuration for dropping an emission amount (luminance) of the light emitting device Le of the sensor Se. More specifically, in this Embodiment, it is set to decrease a voltage value of digital voltage output from the DA output port (see FIG. 12) to the DA converter, and instead of decreasing the voltage value of digital voltage output to the DA converter, a resistance value of the resistance R2 shown in FIG. 12 may be set to be large (the resistance value of the resistance R2 shown in FIG. 12 is set at 330Ω, and may be set at a resistance value of about 910Ω.)

Figure 2:
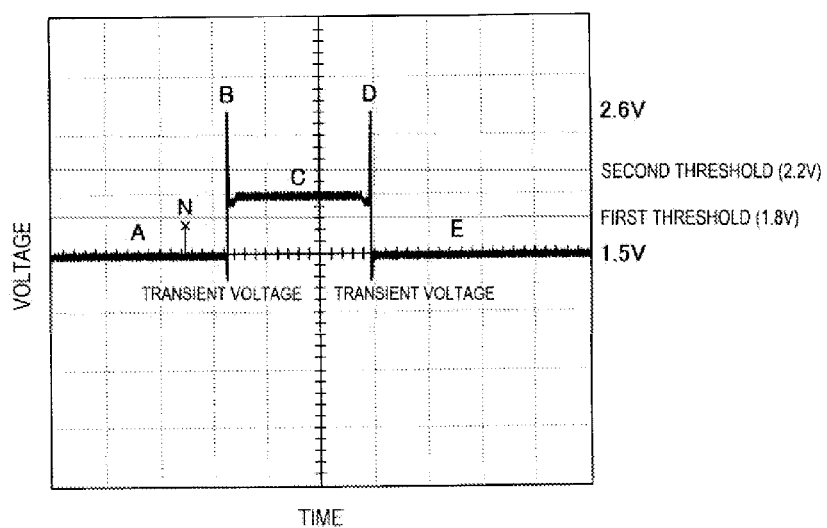
FIG. 2 is a graph schematically showing the output voltage output from a sensor control circuit of the media determining apparatus in the case where a medium is a transparent tube.

FIG. 2 is a graph schematically showing the output voltage output from the sensor control circuit to enable a transparent tube to be detected by dropping the emission amount of the light emitting device Le as described above. In the figure, A is the output Voltage from the sensor control circuit before detecting the transparent tube (before the medium M arrives at a detection position of the sensor Se), B is the output voltage at the time of detecting a front end of the transparent tube, C is the output voltage during detection of the transparent tube, D is the output voltage at the time of detecting a rear end of the transparent tube, and E is the output voltage after detecting the transparent tube (after the medium M passing through the detection position of the sensor Se).

Generally, when light of the light emitting device Le is cut off in the transmission sensor, the output voltage output from the sensor control circuit is high. Therefore, by detecting the output voltage C with a voltage value higher than that of the output voltage A, it is possible to detect the medium M. When the light of the light emitting device Le strikes the front end of the transparent tube, since the front end of the transparent tube has high reflectivity (the transmittance is low), the output voltage B of the sensor control circuit is high (the same as the output voltage E). Further, since the transmittance is higher in the center portion of the transparent tube than in the front end (or rear end) of the transparent tube, the voltage value of the output voltage C is lower than that of the output voltage B (or D). When the emission amount of the light emitting device Le is further dropped, as shown in FIG. 2, it is possible to detect the output voltage (for convenience in description, hereafter, referred to as transient voltage) with a lower voltage than the output voltage A when the output voltage A shifts to the output voltage B (the same when the output voltage D shifts to the output voltage E), and the detection is a clue as to detect the output voltage B.

Since a few fluctuations occur by setting of the voltage value of the digital voltage output to the DA converter and the resistance value of the resistance R2 shown in FIG. 12, with an additional description on the example as shown in FIG. 2 given, in this Embodiment, the output voltage A before detection of the transparent tube and the output voltage after detection of the transparent tube are about 1.5 V±0.2 V, the output voltage B in detection of the front end of the transparent tube and the output voltage D in detection of the rear end are about 2.6 V, and the output voltage C during detection of the transparent tube is about 2.0 V.

Figure 3:
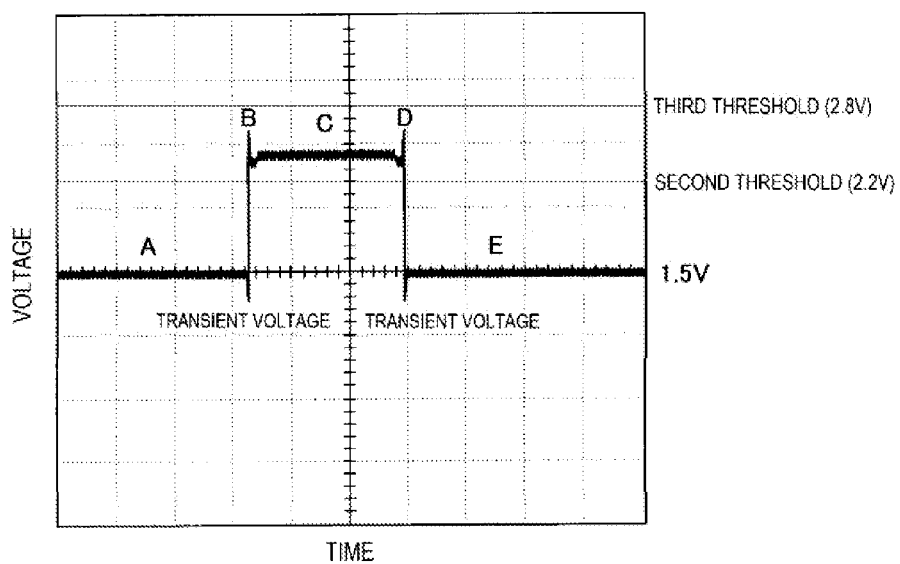
FIG. 3 is a graph schematically showing the output voltage output from the sensor control circuit of the media determining apparatus in the case where a medium is a translucent tube.
Figure 4:
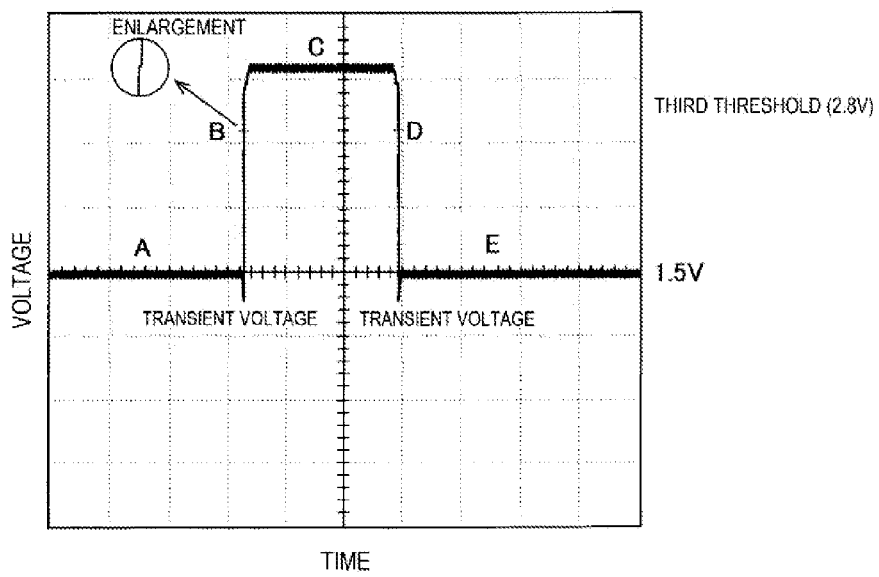
FIG. 4 is a graph schematically showing the output voltage output from the sensor control circuit of the media determining apparatus in the case where a medium is a white tube.

On the other hand, FIG. 3 is a graph schematically showing the output voltage output from the sensor control circuit in the case where the medium M is a translucent tube, and FIG. 4 is a graph schematically showing the output voltage output from the sensor control circuit in the case where the medium M is a white tube (non-transparent body). In the figures, A to E are the same output voltages as in FIG. 2. Herein, the respect to note is that the output voltage C (see FIG. 3) during detection of the translucent tube is higher than the output voltage C during detection of the transparent tube as shown in FIG. 2, and that the output voltage C (see FIG. 4) during detection of the white tube is higher than the output voltage C during detection of the translucent tube. Further, the output voltage C (see FIG. 3) during detection of the translucent tube is lower than the output voltage B at the time of detection of the front end of the translucent tube (and output voltage D at the time of detection of the rear end of the translucent tube) as in the transparent tube as shown in FIG. 2, and in contrast thereto, the output voltage C (see FIG. 4) during detection of the white tube is different from the cases of transparent and translucent tubes as shown in FIGS. 2 and 3, and is higher than the output voltage B at the time of detection of the front end of the white tube (and output voltage D at the time of detection of the rear end of the translucent tube).

Accordingly, by comparing output voltages A to C, it is possible to determine transparency of the medium M. In other words, it is possible to determine that the medium M is a transparent body (transparent tube or translucent tube in the case of the example) when the output voltage C is higher than the output voltage A while being lower than the output voltage B, and it is possible to determine that the medium M is a non-transparent body (white tube in the case of the example) when the output voltage C is higher than the output voltage A, while being higher than the output voltage B. In addition, in the case where the output voltage C and output voltage B are almost equal (for example, output voltage C=output voltage A±0.2 V), the sampling data is regarded as noise.

(Operation)

The operation of the media determining apparatus 10 of this Embodiment will be described next with emphasis on the CPU of the microprocessor MP.

When a determination start command is input from the input section, the CPU drives the stepping motor Mr, and executes a media determining routine to determine transparency of the medium M. The output voltage output from the sensor control circuit is once stored in the RAM functioning as a buffer, and the CPU reads the output voltages stored in the RAM sequentially to identify the above-mentioned output voltages A to E.

Figure 5:
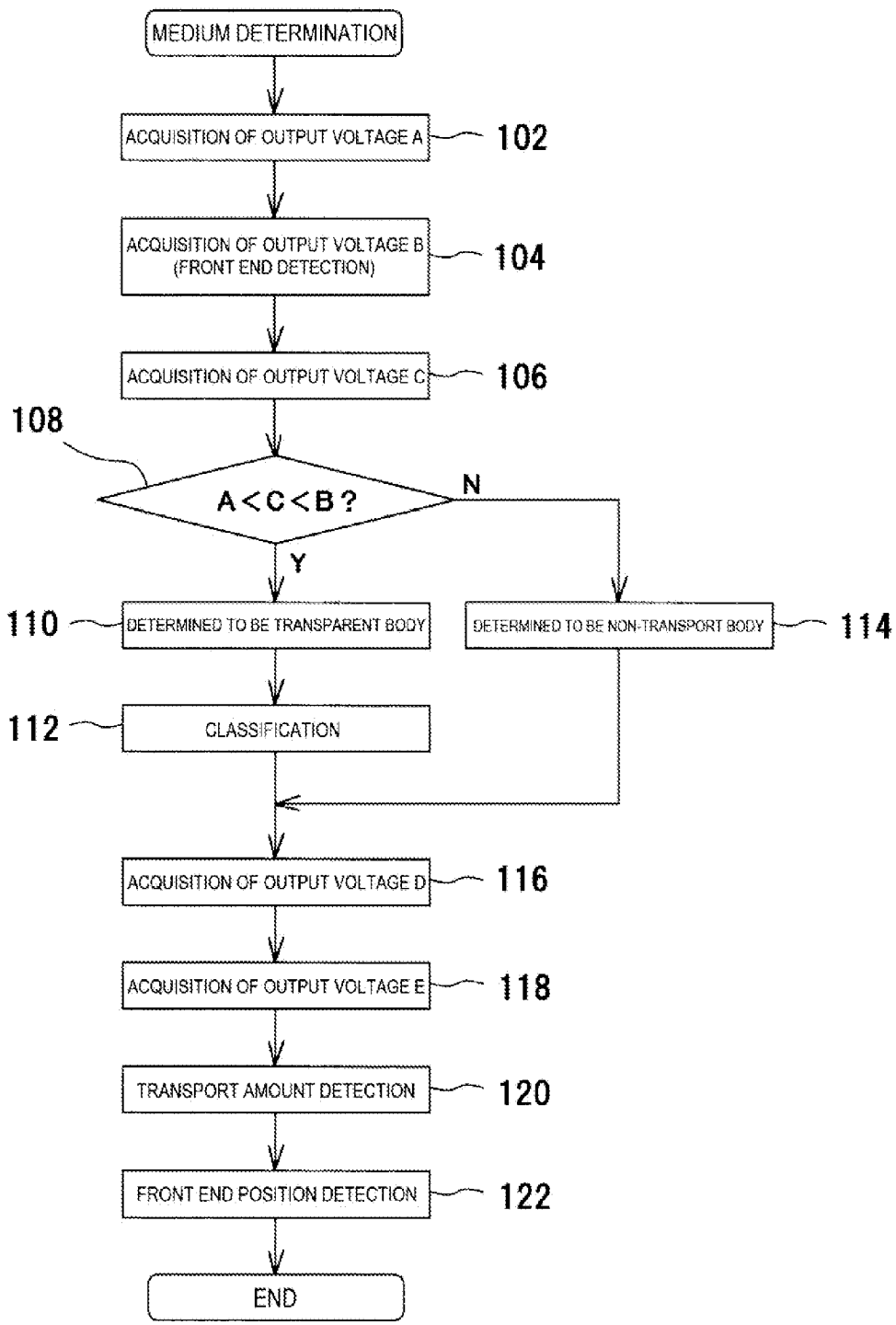
FIG. 5 is a flowchart of a media determining routine executed by a CPU of a microprocessor constituting a control section of the media determining apparatus of the Embodiment.

As shown in FIG. 5, in the media determining routine, in step 102, the CPU acquires (detects) the output voltage A before detection of the medium as shown in FIGS. 2 to 4. Herein, the respect to consider is that there is the case where the output voltage (hereinafter, referred to as sampling data) stored in the RAM includes noise. It is possible to discriminate between the noise and the output voltage A by checking the sampling data a plurality of times. In other words, when the sampling data is once a high voltage and the subsequent voltage returns to the prior voltage, it is possible to regard the high output voltage as noise (see character N in FIG. 2). In addition, as shown in FIG. 2, a first threshold (for example, 1.8 V) is beforehand set, and noise may be regarded in the case where the sampling data is a voltage lower than the first threshold.

Next, in step 104, the CPU acquires the output voltage B in detection of the front end of the medium M. As described above, the transient voltage with a voltage lower than the output voltage A is detected when the output voltage A shifts to the output voltage B. In detecting the output voltage (sampling data) sufficiently higher than the output voltage A after detecting the transient voltage, the CPU acquires the output voltage as the output voltage B in detection of the front end of the medium M. For example, the CPU determines whether or not the voltage is higher than a second threshold (for example, 2.2 V) exceeding the voltage value of the first threshold as described above, and may regard the highest output voltage as the output voltage B among output voltages higher than the second threshold. In addition, by acquiring (detecting) the output voltage B, the CPU is capable of grasping that the front end of the medium M transported with the transport section 11 arrives at a detection position of the sensor Se.

In next step 106, the CPU acquires the output voltage C during detection of the medium M. As shown in FIG. 2, since the transmittance of the light emitted from the light emitting device Le is varied according to the shape of the front end (cut surface) of the medium M immediately after detecting the output voltage B, the output voltage output from the sensor Se is also slightly varied. Therefore, the CPU may determine whether or not the sampling data is a stable voltage (for example, voltage within ±0.2 V) continuously, and when the sampling data is a stable voltage, acquire (detect) the sampling data as the output voltage C. At this point, since there is the case where noise is included, it is preferable to check the sampling data a plurality of times, and when the sampling data is lower than the first threshold, the data may be eliminated as noise from data in acquiring the output voltage C.

Next, in step 108, the CPU compares output voltages A to C acquired in steps 102 to 104 to judge whether or not the relationship is A<C<B. In an affirmative judgement, in next step 110, the CPU judges that the medium M is a transparent body (transparent tube or translucent tube) (also see FIG. 2).

In next step 112, by comparing a beforehand set threshold with the output voltage C, the CPU classifies transparency of the medium M. In addition, "classification" means to sort the extent of transparency. As this threshold, for example, it is possible to use the above-mentioned second threshold (2.2 V), and when the output voltage C is a voltage less than the second threshold, the medium M is determined to be the transparent body (transparent tube) (classified into the transparent body), while being determined to be the translucent body (translucent tube) when the output voltage C is a voltage of the second threshold or more (classified into the translucent body) (also see FIGS. 2 and 3). At this point, in consideration of the above-mentioned first threshold and a beforehand set third threshold (for example, 2.8 V) also, the medium M may be determined to be the transparent body when first threshold≤output voltage C<second threshold, while being determined to be the translucent body when second threshold≤output voltage C<third threshold.

On the other hand, in a negative judgment (A<B≤C) in step 108, the CPU determines that the medium M is the non-transparent body (white tube) in step 114 (also see FIG. 4), and proceeds to next step 116.

With consideration given to the above-mentioned third threshold also, the CPU may determine that the medium M is the non-transparent body (white tube) when output voltage C≥third threshold. Therefore, although the above-mentioned description illustrates mainly the example of determining transparency of the medium M by comparing output voltages A to C, it is also possible to determine transparency of the medium M using the first to third thresholds. In other words, the CPU may determine as noise when the output voltage is less than the first threshold, determine that the medium M is the transparent body when first threshold≤output voltage C<second threshold, determine that the medium M is the translucent body when second threshold≤output voltage C<third threshold, and determine that the medium M is the non-transparent body when third threshold<output voltage C.

Herein, the significance of the above-mentioned "transient voltage" will be described. The transient voltage appears when the emission amount of the light emitting device Le is dropped as in this Embodiment. Further, in the case where the medium M is the transparent body or translucent body, as shown in FIGS. 2 and 3, since the relationship of output voltage A<output voltage C<output voltage B holds, the significance of detecting the transient voltage is small in acquiring the output voltage B (it is possible to accurately acquire the output voltage B even without detecting the transient voltage.) However, as shown in FIG. 4, in the case where the medium M is the non-transparent body, since the relationship of output voltage A<output voltage B<output voltage C holds, unless there is a trigger to detect the output voltage B, it is hard to determine whether the sampling data is the output voltage B, noise or output voltage C. Accordingly, in the case where it is uncertain whether the medium M is the transparent body (including the translucent body) or the non-transparent body, the transient voltage is mainly used to acquire the output voltage B in detection of the front end of the non-transparent body. In other words, in the case where front end detection of the medium M is not required, by using the first to third thresholds as described above, it is possible to determine transparency of the medium M. In addition, a threshold may be provided to detect the transient voltage.

In steps 116 and 118 of FIG. 5, as in steps 104 and 102, the CPU acquires the output voltage D in detection of the rear end of the medium M and the output voltage E after detection of the rear end of the medium M, respectively. In acquiring the output voltage D, in a procedure opposite to that shown in step 104, the CPU detects the transient voltage, and acquires the output voltage D. In other words, after detecting the transient voltage, the output voltage D can be identified from the already read output voltage. By acquiring (detecting) the output voltage D, the CPU is capable of grasping that the rear end of the medium M transported with the transport section 11 arrives at the detection position of the sensor Se. At this point, without acquiring (detecting) the output voltage D, after acquiring the output voltage C, the CPU may detect the rear end of the medium M when the sampling data is the same voltage as the output voltage A. In addition, there is the case where it is not necessary to detect (it is not possible to detect) the rear end depending on the medium M, and such an example will be described later (see the Example).

In next step 120, the CPU detects a transport amount of the medium M up to the present time from the time of acquiring the output voltage B in detection of the front end of the medium M in step 104 (from the time the front end of the medium M arrives at the detection position of the sensor Se). In this Embodiment, the CPU counts the number of pulses sent to the stepping motor Mr via the driver up to the present time, using the time of acquiring the output voltage B in detection of the front end of the medium M in step 104 as a starting point, and detects the number of counted pulses as the transport amount of the medium M, and an encoder may be disposed in the roller 12 or gear unit 13 so as to detect as the transport amount of the medium M based on output (the number of revolutions) from the encoder. In step 122, the CPU detects the current front end position of the medium M from the detected transport amount of the medium M, and finishes the media determining routine. In addition, in this Embodiment, a time difference is extremely small between the time the medium M arrives at the detection position of the sensor Se and the time the CPU acquires the output voltage B, and in the case of using an AD converter of low velocity, it is preferable to correct the time difference.

(Effects and Others)

The effects and others of the media determining apparatus 10 of this Embodiment will be described next.

In the media determining apparatus 10 of this Embodiment, using the sensor Se having the light emitting device Le and light receiving device Lr, the CPU of the microprocessor MP compares output voltages A to C output from the sensor control section (sensor Se) to determine transparency of the medium M, and it is thereby possible to determine the transparency of the medium M at low cost.

Further, in the media determining apparatus 10 of this Embodiment, using the sensor Se having the light emitting device Le and light receiving device Lr, the CPU of the microprocessor MP compares output voltages A to C output from the sensor control section (sensor Se) to detect the front end position of the medium M, and it is thereby possible to detect the front end position of the medium M at low cost irrespective of whether the medium M is transparent or non-transparent. At this point, in the media determining apparatus 10, the emission amount of the light emitting device Le of the sensor Se is dropped to detect the transient voltage (see FIGS. 2 to 4), and it is thereby possible to detect the output voltage B in detection of the front end of the medium M i.e. the front end of the medium M while eliminating noise irrespective of whether the medium M is transparent or non-transparent.

Furthermore, in the media determining apparatus 10 of this Embodiment, since the light emitting device Le and light receiving device Lr are arranged to be inclined with respect to the transport direction of the medium M and the direction orthogonal to the transport direction, it is possible to detect the front end position of the medium M transported with the transport section 11 with accuracy.

In addition, this Embodiment exemplifies transparent, translucent and white (non-transparent) tubes as the medium M, but the present invention is not limited thereto. For example, the invention is applicable to media such as transparent, translucent and non-transparent acrylic plates, labels (films), OHP films (sheets) and the like which have the front end. Further, as a matter of course, although the white tube is exemplified as the non-transparent body, it is possible to similarly detect other color tubes. Furthermore, the above-mentioned first to third thresholds may be changed corresponding to the type of medium M (for example, tube, acrylic plate, film and the like). In this Embodiment, since the type of medium M is input from the input section, the CPU may read beforehand set first to third thresholds corresponding to the input type of medium M.

Further, this Embodiment exemplifies the media determining apparatus 10, but the present invention is not limited thereto. Since the media determining apparatus of this Embodiment is capable of detecting the front end position of the medium M (step 122), it is possible to configure a media sorting apparatus by continuously charging transparent, translucent and non-transparent media M into the transport path P, and varying a transport destination of the medium M to the downstream side of the transport path P corresponding to a determination (classification) result of transparency (transparence, translucence and non-transparence) of the medium M. Further, when liquid is put, by noting that the refractive index is changed to change a light receiving amount of the sensor, for example, it is also possible to determine whether a transparent PET bottle is empty or filled or what the liquid (with transparency of which extent) is.

Furthermore, this Embodiment shows the example of determining whether the medium M is a transparent body or a translucent body with the single second threshold (see FIGS. 2 and 3), and a plurality of thresholds may be provided. In such an aspect, instead of a choice between two alternatives of whether the medium M is a transparent body or a translucent body, it is possible to determine (classify) media having optical transparency more finely, and for example, it is possible to configure as an inspection apparatus for inspecting the optical transparency of the medium M.

Still furthermore, this Embodiment exemplifies the media determining apparatus 10, but the present invention is not limited thereto, and it is possible to widely apply as a media transport apparatus of media including the transparent body and the translucent body. For example, in general business equipment such as a printer, copier, facsimile and ADF, it is possible to perform front end detection of transported transparent sheets and like with accuracy. Further, when the sensor Se is disposed at opposite end portions (two portions) of the transport path of transparent sheets and the like, it is possible to detect skew of the front end of the transported transparent sheet and the like with accuracy. Furthermore, since the present invention enables the front end position of the medium to be detected, it is possible to apply to a cut apparatus and the like to cut the transparent body and the like.

Figure 6:
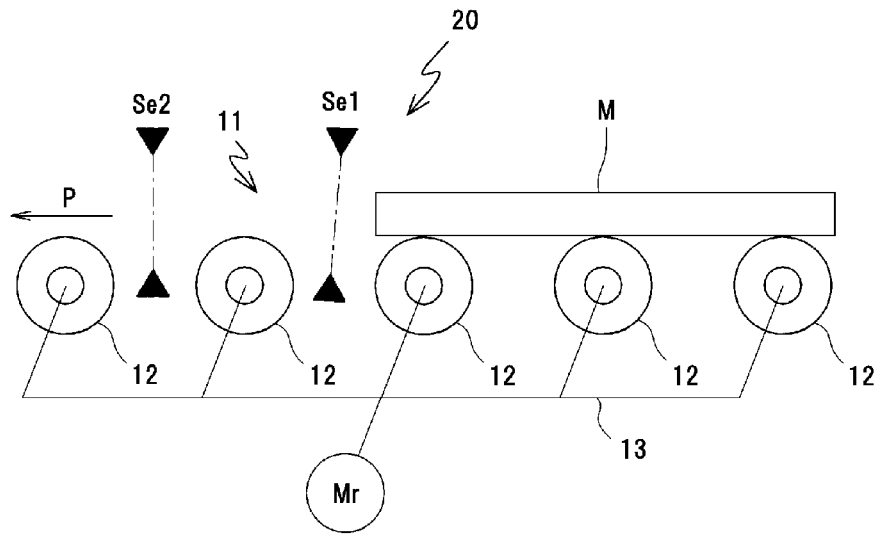
FIG. 6 is a side elevational view schematically illustrating a configuration of a media transport apparatus of an Embodiment to which the present invention is applicable.

Moreover, the media determining apparatus 10 of this Embodiment shows the example of determining transparence, translucence or non-transparence of the medium M with the output voltage output from the single sensor Se, but the present invention is not limited thereto. FIG. 6 illustrates a configuration of a media transport apparatus 20 to which the invention is applicable. The respect different from the media determining apparatus 10 as shown in FIG. 1 is that a sensor is comprised of two sensors of first sensor Se1 to determine transparency of the medium M and second sensor Se2 to perform front end detection of the medium M. The second sensor Se2 is disposed on the downstream side of the first sensor Se1 in the medium transport direction. The light emitting device Le and light receiving device Lr constituting the first sensor Se1 are arranged while being inclined with respect to the direction orthogonal to the transport direction of the medium M, in contrast thereto the light emitting device Le and light receiving device Lr constituting the second sensor Se2 are arranged in the direction orthogonal to the transport direction of the medium M, and the significance will be described later (see the Example <Sensor>).

The first sensor Se1 and second sensor Se2 are the same sensors as the sensor Se constituting the media determining apparatus 10, and as the sensor control circuit, first sensor control circuit and second sensor control circuit are provided respectively corresponding to the first sensor Se1 and second sensor Se2. In the media transport apparatus 20, control with the CPU Of the microprocessor MP is performed on the processing of steps 102 to 114 in FIG. 5 mainly with respect to the output voltage output from the first sensor control circuit, and is performed on the processing of steps 102 to 106 and 116 to 122 in FIG. 5 mainly with respect to the output voltage output from the second sensor control circuit. The important respect is that the CPU compares the output voltages A to C output from the first sensor control circuit to determine transparency of the medium M, corresponding to the determination result changes the voltage to output to the DA converter of the second sensor control circuit, and thereby adjusts an emission amount of the light emitting device Le constituting the second sensor Se2.

The first sensor control circuit adopts the configuration of dropping the emission amount of the light emitting device Le constituting the first sensor Se1 as in the sensor control circuit of the media determining apparatus 10. From a different point of view, dropping the emission amount of the light emitting device Le means dulling sensitivity as the control circuit of the first sensor Se1, and therefore, it is not necessary that the emission amount of the light emitting device Le of the second sensor Se2 is the same as the emission amount of the light emitting device Le of the first sensor Se1.

In the media transport apparatus 20, since the emission amount of the light emitting device Le constituting the second sensor Se2 is adjusted corresponding to transparency of the medium M, the output voltage output from the second sensor control circuit (light receiving device Lr of the second sensor Se2) is stabilized, it is thereby possible to detect the front end of the medium M with accuracy, and even in the case where the medium M is large (even in the case where a distance between the light emitting device Le and the light receiving device Lr is long), it is possible to detect the front end.

Figure 7:
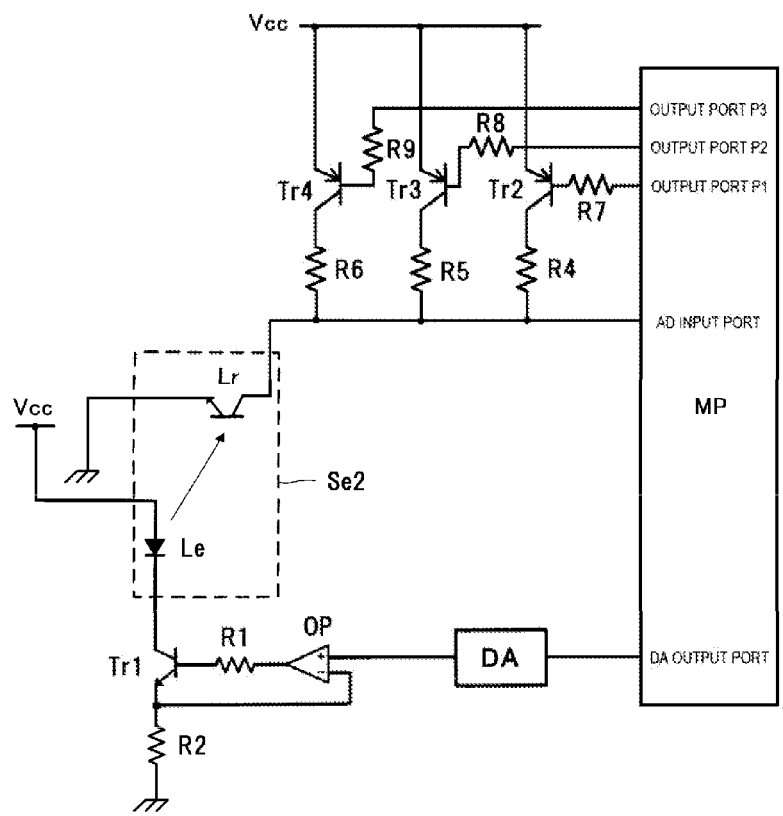
FIG. 7 is a circuit diagram illustrating another Embodiment of the sensor control circuit applicable to a second sensor of the media transport apparatus.

Further, in the case of providing the first sensor Se1 and second sensor Se2 as described above, in the sensor control circuit of the second sensor Se2, instead of the resistance R3 of the sensor control circuit as shown in FIG. 12, as shown in FIG. 7, by controlling on and off of switch devices (transistors Tr2 to Tr4) respectively constituting a plurality of switch resistance circuits (transistors Tr2 to Tr4 and resistances R4 to R6) (outputting a high-level signal to one of output ports P1 to P3) corresponding to transparency of the medium, it is possible to prevent a waveform output from the sensor Se2 from collapsing, and to detect the front end position of the medium M with higher accuracy. In addition, details of such an aspect are disclosed in Patent Document 5 as described above.

Furthermore, this Embodiment exemplifies the transmission sensor as the sensor Se, but the present invention is not limited thereto, and a reflection sensor may be used. Still furthermore, as shown in FIG. 12, this Embodiment shows the example where the voltage of the collector of the phototransistor constituting the light receiving device Lr is made the output voltage of the sensor control circuit (sensor Se), but the present invention is not limited thereto, and Vcc may be connected to the collector of the phototransistor while the resistance R3 may be connected to between the emitter of the phototransistor and GND so that the voltage of the emitter of the phototransistor is made the output voltage of the sensor control circuit. In such an aspect, the waveform of the output voltage output from the sensor Se is inverted in the vertical direction of FIGS. 2 to 4 and FIGS. 13 and 14.

Moreover, this Embodiment shows the example where the light emitting device Le and light receiving device Lr of the sensor Se are arranged to be inclined with respect to the transport direction of the medium M and the direction orthogonal to the transport direction, but the present invention is not limited thereto, and the light emitting device Le and light receiving device Lr may be arranged to be inclined with respect to at least one of the transport direction of the medium M and the direction orthogonal to the transport direction.

[Example]

Described next is the Example in which the present invention is applied to a printer capable of printing characters and like arbitrarily on a long printing medium such as a label and tube according to the above-mentioned Embodiment.

(Configuration)

<Entire Configuration>

Figure 8:
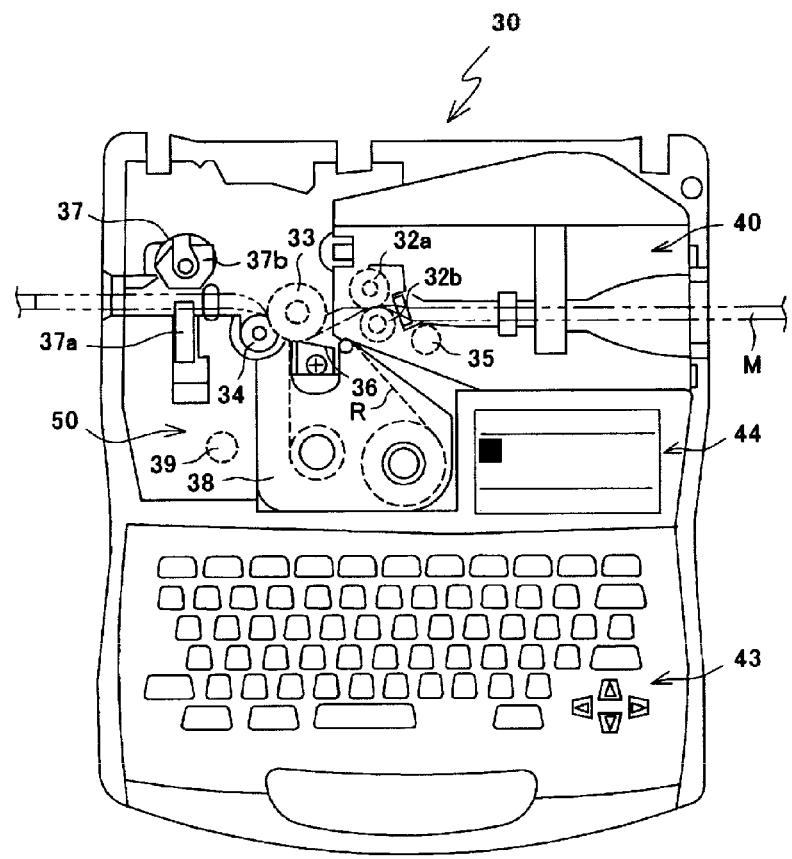
FIG. 8 is an external view of a printer of an Embodiment.

As shown in FIG. 8, a printer 30 of this Example is configured to be portable as in notebook computers, and is broadly provided with an input section 43 having a keyboard and input control section, a display section 44 having an LCD and display control section, a printing section 50 that performs printing processing on a printing medium M via an ink ribbon R by heating selectively heating elements lined in the main scanning direction constituting a thermal head 36, a cut section 37 provided on the downstream side of the printing section 50 in the medium transport direction to perform cutting processing on the printing medium M, and a control section 45 (see FIG. 11) that controls each of the sections. Further, the printer 30 has a cassette insertion section in which an ink ribbon cassette 38 is inserted.

<Input Section>

The input section 43 has function keys, character numeric symbol keys, space key, conversion key, cross-direction keys, return key and the like almost equal to notebook computers, and an operator operates these keys and is thereby capable of inputting the type of printing medium M, size, setting conditions and the like.

<Display Section>

The LCD of the display section 44 is divided into three display areas of a various information display area that displays an input mode and the like, a character information display area that displays characters, numerics and symbols (hereinafter, abbreviated as character) input from the input section 43, and a parameter display area that displays the character size and the like, and the various information display area and parameter display area are disposed respectively above and below the character information display area.

<Printing Section>

The printing section 50 has transport rollers 32a, 32b to transport the printing medium M, a platen roller 33 disposed opposite the thermal head 36 on the downstream side of the transport rollers 32a, 32b, and a pinch roller 34 disposed on the downstream side of the platen roller 33 to be opposed to the platen roller 33.

The ink ribbon R exists between the platen roller 33 and the thermal head 36. The ink ribbon R is stored inside the ink ribbon cassette 38, is supplied from a supply reel of the ink ribbon cassette 38, and is wound up around a wind-up reel. In addition, in this Example, a single-color ink ribbon of Bk (Black) is used for the ink ribbon R.

On the upstream side of the transport rollers 32a, 32b is disposed a stepping motor 35 which rotates and drives the transport roller 32a, platen roller 33 and wind-up reel of the ink ribbon cassette 38 via gears not shown, and on one side (left side in FIG. 1) of the ink ribbon cassette 38 while being on one side (lower side in FIG. 1) of the cut section 37 is disposed a stepping motor 39 that shifts the thermal head 36 between a retract position retracted from a medium transport path and a printing position to come into press-contact with the platen roller 33 via gears and cam not shown.

FIG. 8 illustrates a state in which a tube is inserted as the printing medium M. With the description given according to this example, by bringing the thermal head 36 into press-contact with the printing medium M with the ink ribbon R of the ink ribbon cassette 38 therebetween, while heating selectively the healing elements constituting the thermal head 36, the ink of the ink ribbon R is fused to print character lines on the printing medium M for each line. The thermal head 36 is configured integrally with a head control section that controls the thermal head 36. In addition, in the following description, except the required case, the description is given assuming that a tube is used for the printing medium M according to the example of FIG. 8.

<Cut Section>

The cut section 37 to cut the printing medium M is disposed on the downstream side of the pinch roller 34. The cut section 37 has a cutter blade 37a and cutter blade receiving base 37b. The cutter blade receiving base 37b is provided with a whole-cut surface comprised of a flat surface and a half-cut surface having protrusions in opposite end portions, and by setting the whole-cut surface or half-cut surface approximately perpendicularly to the cutter blade 37a, it is possible to perform all-cut processing and half-cut processing of the printing medium M. Herein, the half-cut means partially cutting the printing medium M irrespective of the ratio of the cut. Further, the half-cut method may be changed according to the type of printing medium M. For example, in the case where the printing medium M is a label with releasing paper, only the label may be cut without cutting the releasing paper, and in the case of roll paper or ribbon tape, the medium may be perforated.

By operating the cutter blade 37a (shifting from a retract position to a proceed position) at the time printing with the thermal head 36 is finished and the medium is transported to the downstream side by a predetermined length, it is possible to obtain the printing medium M with a length desired by the operator. In addition, in this Embodiment, the rotation drive force of the stepping motor 39 is used for operation of the cutter blade 37a via a cam and the like not shown, while being used also for changing the surface of the cutter blade receiving base 37b via another cam and the like.

<Attachment Section>

The printer 30 is configured to be able to perform printing and cutting processing on various printing media M by changing an attachment to attach to an attachment section

Figure 10A:
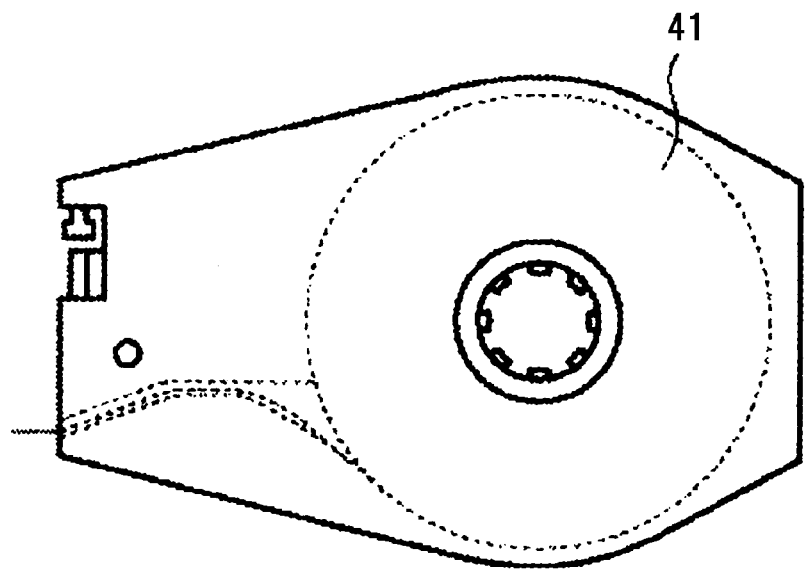
FIGS. 10A and 10B contain plan views of attachments attachable to an attachment section of the printer of the Embodiment, where
Figure 10B:
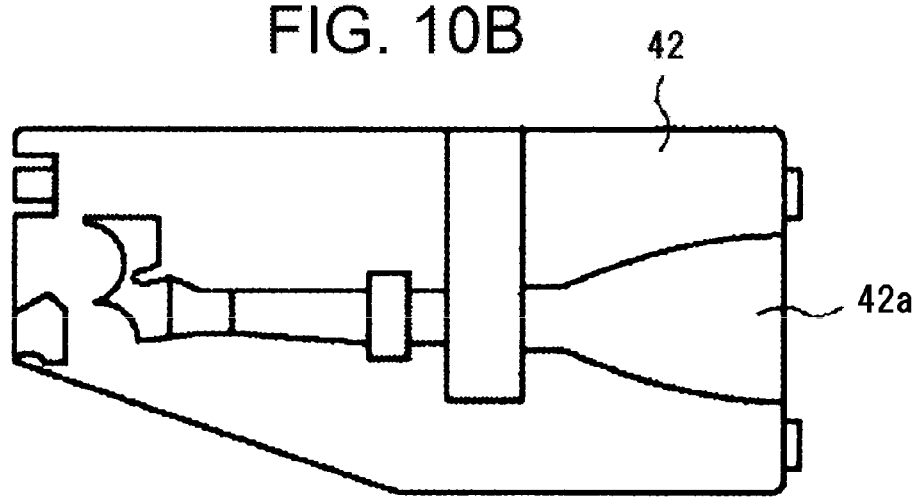

40. FIGS. 10A and 10B show examples of attachments for label cassette and tube. For example, in the case of attaching a label cassette 41 as shown in FIG. 10A to the attachment section 40, the label with releasing paper is pulled out of the inside of the cassette, and it is possible to perform printing and cutting processing on the label. Further, in the case of attaching a tube attachment 42 as shown in FIG. 10B to the attachment section 40, by inserting a tube from a tube insertion opening 42*a*, it is possible to perform printing and cutting processing on the tube.

<Sensor>

Figure 9:
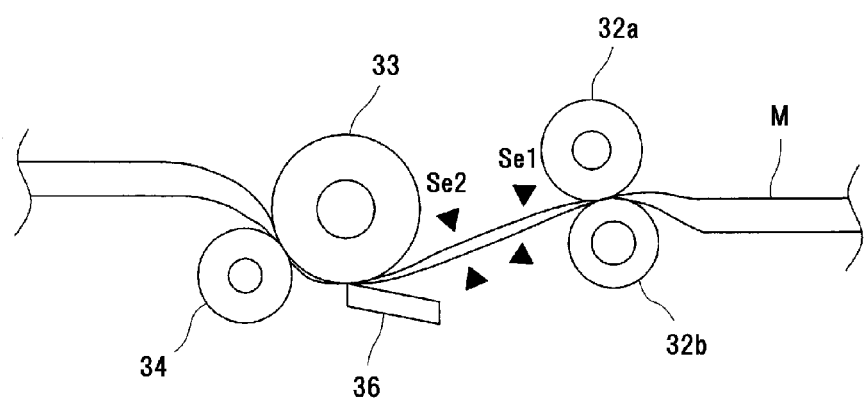
FIG. 9 is a partial configuration view illustrating a configuration in the vicinity of a printing section of the printer of the Embodiment.

As shown in FIG. 9, the first sensor Se1 to detect transparency of the printing medium M is disposed on the downstream side of the transport rollers 32*a*, 32*b*. The first sensor Se1 is a transmission sensor, and the light emitting device Le (LED) and light receiving device Lr (phototransistor) constituting the first sensor Se1 are disposed obliquely with respect to the direction orthogonal to (crossing) the transport direction of the printing medium M. The second sensor Se2 to perform front end detection of the medium M is disposed on the downstream side of the first sensor Se1 and on the upstream side of the thermal head 36 and platen roller 30 constituting the printing section 50. The second sensor Se2 is a transmission sensor, and to detect the front end of the transported printing medium M with high accuracy, as distinct from the first sensor Se1, the light emitting device Le (LED) and light receiving device Lr (phototransistor) constituting the second sensor Se2 are disposed in the direction orthogonal to the transport direction of the printing medium M.

<Control Section>

Figure 11:
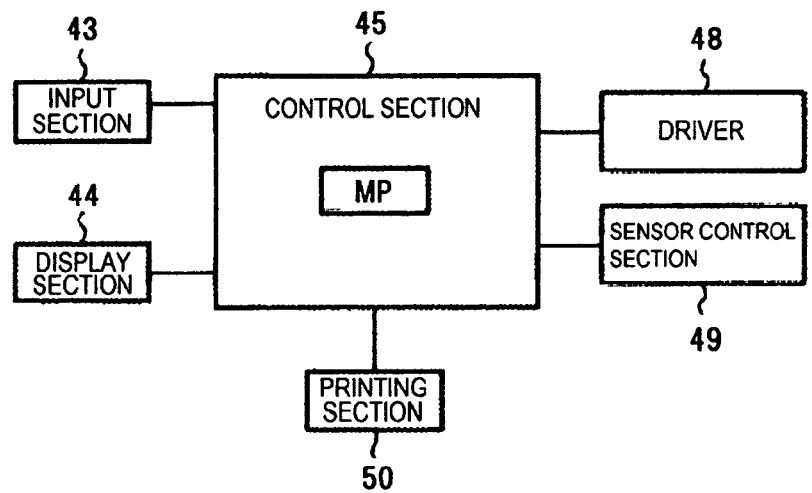
FIG. 11 is a block diagram illustrating a control section and connection system of the printer of the Embodiment.

As shown in FIG. 11, the control section 45 is comprised of the microprocessor MP having the CPU, ROM and RAM. External buses are connected to the control section 45. To the external buses are connected the input section 43, display section 44, thermal head 36 of the printing section 50, driver 48 that controls operation of stepping motors 35, 39, and sensor control section 49 having the above-mentioned first and second sensor control circuits and the like.

The sensor control section 49 has a first sensor control section that acquires the output voltage output from the first sensor Se1, and a second sensor control section that acquires the output voltage output from the second sensor Se2. The first sensor control section has the circuit configuration as shown in FIG. 12, and the second sensor control section has the circuit configuration as shown in FIG. 7. In addition, as described above, the first sensor control section adopts the configuration for dropping the emission amount of the light emitting device Le.

Further, the control section 45 has a buffer and interface not shown, and is capable of being connected to a higher apparatus such as a personal computer, for example, via the external bus. Therefore, instead of input from the input section 43, the operator is also capable of inputting from the higher apparatus, and further, by attaching an external storage apparatus such as a RAM card and USB, is also capable of using data stored in the external storage apparatus.

(Operation)

Next, operation of the printer 30 of this Example will be described briefly with emphasis on the CPU (hereinafter, referred to as CPU) of the microprocessor MP constituting the control section 45.

When power is supplied to the printer 30, programs and program data stored in the ROM are decompressed in the RAM, and after performing initial setting processing to shift each of the above-mentioned sections to a predetermined home position, the CPU waits for input of printing direction information and cut direction information from the input section 43 by the operator.

When these pieces of information are input, the CPU generates printing data according to the input printing direction information, and waits for a printing start instruction from the operator. Upon receiving the printing start instruction by the operator pressing down a predetermined button (for example, entry button) of the input section 43, the CPU drives the stepping motor 35 to start transport of the printing medium M, and judges (determines transparency of the printing medium M) that the printing medium M is a transparent body, translucent body or non-transparent body by referring to the output voltage (sampling data) output from the sensor Se1, while detecting the front end position of the printing medium M by referring to the output voltage output from the sensor Se2 (also see FIG. 5).

The CPU changes a heat value of the thermal head 36 (printing condition on the printing medium M) corresponding to the transparency of the printing medium M (whether the printing medium M is a transparent body, translucent body or non-transparent body). Such a change in the printing condition is made to enhance printing quality. For example, in the case of assuming that the heat value when the printing medium M is a non-transparent body (for example, white tube without having optical transparency) as 100%, the heat value is set at about 75% to 85% for the translucent body, and is set at about 55% to 65% for the transparent body, but the present invention is not limited thereto. In consideration of also specific heat of the printing medium M, the heat value of the thermal head 36 may be changed corresponding to the type and transparency of printing medium M.

Further, the CPU detects the front end position of the printing medium M by referring to the output voltage output from the sensor Se2, and when the printing medium M arrives at a predetermined position, drives the stepping motor 39 (shifts the thermal head 36 to a printing position) to perform printing processing on the printing medium M. In addition, in this Example, positions of the sensor Se2 and a head portion of the thermal head 36 are known, and the CPU counts the number of pulses output to the stepping motor 35 from the time of detecting the printing medium M by monitoring the output voltage of the second sensor Se2, is thereby capable of grasping the front end position of the transported printing medium M, and therefore, is capable of grasping (controlling) timing for driving the stepping motor 39 (shifting the thermal head 36 to the printing position to come into press-contact with the platen roller 33) with accuracy.

After shifting the thermal head 36 to the printing position, the CPU outputs to the driver 48 for each line according to the printing data. The printing medium M is transported to the downstream side on the medium transport path by the rotation drive force of the transport rollers 32*a*, 32*b*, platen roller 33 and pinch roller 34, and desired characters are printed in the printing section 50.

When the printing processing on the printing medium M with the printing section 50 (thermal head 36) is finished, the CPU shifts the thermal head 36 to the retract position retracted from the medium transport path, and by referring to a third sensor (transmission sensor having the light emitting device Le and light receiving device Lr) disposed on the downstream side of the pinch roller 34, judges whether or not the front end of the printing medium M is positioned on the downstream side from the position of the sensor. In an affirmative judgement, the CPU rotates the transport rollers 32*a*, 32*b*, platen roller 33 and pinch roller 34 backward to transport backward by a predetermined distance so that the front end of the printing medium M is positioned on the upstream side from the position of the sensor, and then, rotates the transport rollers 32a, 32b, platen roller 33 and pinch roller 34 forward to transport the printing medium M to the cut section 37 side. In a negative judgement, the CPU rotates the transport rollers 32a, 32b, platen roller 33 and pinch roller 34 forward to transport the printing medium M to the cut section 37 side without other operation. In addition, a sensor control circuit of the third sensor may be the same as the sensor control circuit (see FIG. 7) of the second sensor Se2 or may be the same as the sensor control circuit as shown in FIG. 12.

Further, the CPU positions a receiving surface of the cutter blade receiving base 37b so that the surface (whole-cut surface, half-cut surface) directed by the cut direction information faces a position opposed to the cutter blade 37a via the medium transport path according to the cut direction information, for a period up to this point in time from the time the printing direction information and cut direction information is input from the operator.

When the front end of the printing medium M passes through the position of the cutter blade 37b and a cut position of the printing medium M is transported to the position of the cutter blade 37b, the CPU once halts driving of the rollers 32a, 32b, platen roller 33 and pinch roller 34 to halt transport of the printing medium M, moves the cutter blade 37a toward the cutter blade receiving base 37b, and thereby cuts the printing medium M. By referring to output from the third sensor disposed on the downstream side of the pinch roller 34, the CPU monitors whether or not the front end of the printing medium M arrives at the position of the sensor, and by counting the number of output pulses to the stepping motor 39 with reference to the position of the sensor, is capable of grasping the relationship of the position of the front end of the printing medium M with the position of the cutter blade 37a i.e. the cut position.

Next, the CPU resumes driving of the rollers 32a, 32b, platen roller 33 and pinch roller 34, and further transports the printing medium M to the downstream side by a predetermined distance to discharge from the printer 30. Then, after a lapse of predetermined time, the CPU halts driving of the rollers 32a, 32b, platen roller 33 and pinch roller 34, and finishes operation based on the input printing/cut direction information. In addition, further, after a lapse of predetermined time, in order to prevent the printing medium M from curling by the printing medium M positioning in a curve portion on the medium transport path, the CPU drives the rollers 32a, 32b, platen roller 33 and pinch roller 34, and rewinds the printing medium M to the transport rollers 32a, 32b side.

In the printing apparatus 30 of this Example, using the first sensor Se1 and second sensor Se2 each having the light emitting device Le and light receiving device Lr, the CPU compares the output voltages A to C of the first sensor Se1 and second sensor Se2 to control a printing start on the printing medium M with the printing section 50 (thermal head 36), and it is thereby possible to ensure high printing position accuracy on the printing medium M at low cost irrespective of whether the medium is transparent or non-transparent. Further, in the printing apparatus 30 of this Example, the CPU automatically determines transparency of the printing medium M, it is thereby not necessary to input information on the transparency of the printing medium M, and operation by the operator is made easy. Furthermore, in the printing apparatus 30 of this Example, since the printing condition on the printing medium M is changed corresponding to the transparency of the printing medium M, it is possible to enhance printing quality on the printing medium M.

In addition, the above-mentioned Example exemplifies the direct printing scheme printer 30 for directly forming an image on the printing medium M using the ink ribbon R, but the present invention is not limited thereto. For example, the invention is applicable to an indirect printing scheme printing apparatus for forming an image on an intermediate transfer medium using an ink ribbon, and transferring the image formed on the intermediate transfer medium to the printing medium. Further, the above-mentioned example exemplifies the ink ribbon cassette 38 using the single-color ink ribbon of black for the ink ribbon R, but the present invention is not limited thereto, and for example, the invention is applicable to an ink ribbon cassette using ink ribbons configured by repeating a plurality of color ribbon panels of yellow, magenta, cyan and the like in a face sequential manner, and ink ribbon cassettes storing ink ribbons obtained by adding a black ribbon panel thereto, or adding a protective layer and another color such as silver and gold.

In addition, this application claims priority from Japanese Patent Application No. 2014-147866 incorporated herein by reference.

The invention claimed is:

1. A media determining apparatus comprising:
a transport section adapted to transport a medium;
a single sensor including a light emitting device and a light receiving device to detect the medium; and
a control section adapted to detect the medium transported with the transport section corresponding to an output voltage of the sensor,
wherein the control section determines transparency of the medium by comparing an output voltage A of the sensor before a front end of the medium arrives at a detection position of the sensor, an output voltage B of the sensor when the front end arrives at the detection position, and an output voltage C of the sensor after the medium has transported for a predetermined amount since the front end passed the detection position; and
the control section determines that the medium is a transparent body when the output voltage C is higher than the output voltage A, while being lower than the output voltage B.

2. The media determining apparatus according to claim 1, wherein the control section detects the output voltage B after detecting a voltage lower than the output voltage A.

3. The media determining apparatus according to claim 1, wherein the control section classifies transparency of the medium by comparing a beforehand set threshold with the output voltage C.

4. The media determining apparatus according to claim 3, wherein the transparent body is transparent or translucent, and
the control section determines that the transparent body is transparent when the output voltage C is less than the threshold, and the transparent body is translucent when the output voltage C is equal to or higher than the threshold.

5. The media determining apparatus according to claim 1, wherein the control section determines that the medium is a non-transparent body when the output voltage C is higher than the output voltage B.

6. The media determining apparatus according to claim 1, wherein the sensor is a transmission sensor, and the light emitting device and the light receiving device are arranged to be inclined with respect to a transport direction of the medium transported with the transport section or a direction orthogonal to the transport direction.

7. The media determining apparatus according to claim 1, wherein the control section detects an output voltage of the sensor as the output voltage C when the output voltage is stable within a predetermined range after the output voltage B was detected.

8. A media transport apparatus comprising:
a transport section adapted to transport a medium;
a single sensor including a light emitting device and a light receiving device to detect the medium; and
a control section adapted to detect the medium transported with the transport section corresponding to an output voltage of the sensor,
wherein the control section detects a front end position of the medium by comparing an output voltage A of the sensor before a front end of the medium arrives at a detection position of the sensor, an output voltage B of the sensor when the front end arrives at the detection position, and an output voltage C of the sensor after the medium has transported for a predetermined amount since the front end passed the detection position; and
the control section determines that the medium is a transparent body when the output voltage C is higher than the output voltage A, while being lower than the output voltage B.

9. The media transport apparatus according to claim 8, wherein the control section detects the output voltage B after detecting a voltage lower than the output voltage A.

10. The media transport apparatus according to claim 8, wherein the control section detects the front end position of the medium based on the transport amount of the medium with the transport section up to the present time from the time the front end of the medium arrives at the detection position of the sensor.

11. The media transport apparatus according to claim 8, wherein the control section detects a rear end position of the medium when an output voltage of the sensor is the same voltage as the output voltage A after detecting the output voltage C.

12. The media transport apparatus according to claim 8, wherein the sensor detects transparency of the medium, the media transport apparatus further comprising another sensor disposed on the downstream side of the sensor in a medium transport direction to perform front end detection of the medium, and
the control section determines transparency of the medium by comparing the output voltages A to C of the sensor to adjust an emission amount of a light emitting device constituting the another sensor corresponding to a result of determination.

13. The media transport apparatus according to claim 12, wherein the sensor is a transmission sensor, and the light emitting device and the light receiving device constituting the sensor are arranged to be inclined with respect to the transport direction of the medium transported with the transport section or a direction orthogonal to the transport direction.

14. The media transport apparatus according to claim 8, wherein the control section detects the voltage as the output voltage C when the voltage is stable within a predetermined range after the output voltage B was detected.

15. A printing apparatus comprising:
a transport section adapted to transport a printing medium;
a single sensor including a light emitting device and a light receiving device to detect the printing medium;
a printing section adapted to perform printing processing on the printing medium; and
a control section adapted to detect the printing medium transported with the transport section corresponding to an output voltage of the sensor,
wherein the control section controls a start of printing on the printing medium by comparing an output voltage A of the sensor before a front end of the printing medium arrives at a detection position of the sensor, an output voltage B of the sensor when the front end arrives at the detection position, and an output voltage C of the sensor after the medium has transported for a predetermined amount since the front end passed the detection position; and
the control section determines that the printing medium is a transparent body when the output voltage C is higher than the output voltage A, while being lower than the output voltage B.

16. The printing apparatus according to claim 15, wherein the control section compares the output voltages A to C to determine transparency of the printing medium and, and changes a printing condition on the printing medium with the printing section.

17. A media determining apparatus comprising:
a transport section adapted to transport a medium;
a single sensor including a light emitting device and a light receiving device to detect the medium; and
a control section adapted to detect the medium transported with the transport section corresponding to an output voltage of the sensor,
wherein the control section determines that the medium is a transparent body, when:
an output voltage A of the sensor before a front end of the medium arrives at a detection position of the sensor is lower than a first threshold set beforehand,
an output voltage B of the sensor when the front end arrives at the detection position is higher than a second threshold set larger than the first threshold, and
an output voltage C of the sensor after the medium has transported for a predetermined amount since the front end passed the detection position is in a range between the first threshold and the second threshold.

18. The media determining apparatus according to claim 17, wherein the transparent body is transparent or translucent, and
the control section determines that the transparent body is translucent when the output voltage C is in arrange between the second threshold and a third threshold set larger than the second threshold; and
the control section determines that the medium is a non-transparent body when the output voltage C is higher than the third threshold.

19. A media transport apparatus comprising:
a transport section adapted to transport a medium;
a single sensor including a light emitting device and a light receiving device to detect the medium; and
a control section adapted to detect the medium transported with the transport section corresponding to an output voltage of the sensor,
wherein the control section determines that the medium is a transparent body, when:
an output voltage A of the sensor before a front end of the medium arrives at a detection position of the sensor is lower than a first threshold set beforehand, an output voltage B of the sensor when the front end arrives at the detection position is higher than a second threshold set larger than the first threshold, and an output voltage C of the sensor after the medium has transported for a predetermined amount since the front end passed the detection position is in a range between the first threshold and the second threshold; and the control section detects a front end position of the medium.

20. A printing apparatus comprising:

a transport section adapted to transport a printing medium;

a single sensor including a light emitting device and a light receiving device to detect the printing medium;

a printing section adapted to perform printing processing on the printing medium; and a control section adapted to detect the printing medium transported with the transport section corresponding to an output voltage of the sensor, wherein the control section determines that the printing medium is a transparent body, when:

an output voltage A of the sensor before a front end of the printing medium arrives at a detection position of the sensor is lower than a first threshold set beforehand, an output voltage B of the sensor when the front end arrives at the detection position is higher than a second threshold set larger than the first threshold, and an output voltage C of the sensor after the medium has transported for a predetermined amount since the front end passed the detection position is in a range between the first threshold and the second threshold; and the control section controls a start of printing on the printing medium.

* * * * *